United States Patent [19]

Nakanishi et al.

[11] Patent Number: 4,759,360
[45] Date of Patent: Jul. 26, 1988

[54] LASER COAGULATION SYSTEM

[75] Inventors: Takaji Nakanishi, Toyokawa, Japan; David R. Hennings, Half Moon Bay, Calif.; Masao Niino, Okazaki, Japan

[73] Assignees: Kowa Company Ltd., Aichi, Japan; Coherent Incorporated, Palo Alto, Calif.

[21] Appl. No.: 919,315

[22] Filed: Oct. 14, 1986

[30] Foreign Application Priority Data

Oct. 16, 1985 [JP] Japan .................................. 60-228833

[51] Int. Cl.⁴ ............................................ A61B 17/36
[52] U.S. Cl. .................................... 128/303.1; 128/395
[58] Field of Search ............ 128/4, 6, 303.1, 395–398; 350/271, 615, 623, 637, 607, 286, 613, 616, 626; 362/259

[56] References Cited

U.S. PATENT DOCUMENTS

| 2,699,092 | 1/1955 | Rantsch | 350/286 |
| 3,828,788 | 8/1974 | Krasnou et al. | 128/303.1 |
| 4,164,222 | 8/1979 | Prokherov et al. | 128/303.1 |
| 4,428,035 | 1/1984 | Müller et al. | 362/293 |
| 4,477,720 | 10/1984 | Pearson | 350/607 |
| 4,499,897 | 2/1985 | Roussel | 128/395 |
| 4,520,824 | 6/1985 | Swaniger et al. | 128/395 |
| 4,561,436 | 12/1985 | Munnerlyn | 128/395 |
| 4,597,380 | 7/1986 | Raif et al. | 128/395 |

*Primary Examiner*—Max Hindenburg
*Attorney, Agent, or Firm*—Bruce L. Adams; Van C. Wilks

[57] ABSTRACT

A laser coagulation system adapted for use in an ophthalmological treatment comprises a slit image projector for projecting a slit image into the eyeball of a patient to determine a selected portion of the eyeball to be coagulated, and a laser beam projector for projecting a laser beam onto the selected portion. Both the projectors include a common reflecting means which is divided into two side portions for directing slit light toward the selected portion to be coagulated, and a central portion between the two side portions for directing the laser beam toward the selected portion thereof.

13 Claims, 3 Drawing Sheets

LASER COAGULATION SYSTEM

BACKGROUND OF THE INVENTION

1. Field of the Invention

This invention relates to a laser coagulation system, and more particularly to a laser coagulation system adapted for use in an ophthalmological treatment in which a laser beam from a laser source is radiated into a patient's eye to develop great heat causing thermal coagulation at a predetermined portion of the biological organism in the eyeball of a patient.

2. Description of the Prior Art

There have long been known laser coagulation systems in which during an ophthalmic operation against diseases such as retina detachment, glaucoma, etc., a patient's eye is irradiated with laser energy which is absorbed in a biological organism such as retina to develop thermal coagulation thereon for ophthalmological treatment. For this purpose, the laser coagulation system includes a laser beam projector for producing a laser beam from an argon or krypton laser, the laser beam being condensed to a predetermined diameter, directed toward a predetermined portion of the eyeball to be coagulated, and then focussed thereon as a laser spot for thermal coagulation.

The laser coagulation system further comprises a slit image projector for forming a slit image on the eyeball to illuminate the background and determine the predetermined portion of eyeball to be coagulated, and observation equipment for observing the slit image and laser spot in the eyeball.

In such prior laser coagulation systems, the slit image projector is provided with a mirror for directing the slit image toward the predetermined portion of the eye, while the laser beam projector is provided with a mirror for directing the laser beam toward the predetermined portion thereof. The mirror for the slit image projector is divided into upper and lower portions, behind which the mirror for the laser beam projector is arranged.

In this case, the slit image projector is arranged at the lower portion of the system and projects slit light, which is reflected by the two-divided mirror toward the selected portion of the eye to be coagulated, while the laser beam projector is arranged at the upper portion of the system and emits a laser beam, which is, after the reflection by the mirror, caused to pass through a gap between the upper and lower portions of the two-divided mirror, thereby forming a laser spot in the proximity of the slit image in the eyeball.

Thus, the laser coagulation system in the prior art has the drawback that the laser beam projector constitutes a different system from that of the slit image projector. This disadvantageously leads to a large-sized coagulation system. Furthermore, the mirror for the laser beam projector must be large enough to allow the formation of the laser spot of a greater diameter at portions other than the selected portion to be coagulated in order to provide a reduced energy density causing no coagulation. This also disadvantageously causes the mirror for the slit image projector to become smaller, thus resulting in the formation of a dark and blurred slit image.

In addition, the prior slit image projector employs a Keller illumination in which a lamp filament is imaged on the entrance pupil of a slit imaging lens. In this situation, the two-divided mirror of the slit image projector has a gap between the divided portions, so that the light illuminating the center of the entrance pupil may be caused to pass through the gap which results in reduced intensity of the slit image.

SUMMARY OF THE INVENTION

It is therefore an object of the present invention to provide an improved laser coagulation system capable of making the whole system more compact.

It is another object of the present invention to provide a laser coagulation system capable of producing a bright slit image and providing an improvement in illumination efficiency.

A laser coagulation system according to the invention comprises a slit image projector for projecting a slit image into the eyeball of a patient to determine a selected portion of the eyeball to be coagulated, and a laser beam projector for projecting a laser beam onto said selected portion. The slit image projector and laser beam projector include a common reflecting means, which is divided into side portions for directing slit light toward the selected portion and a central portion for directing the laser beam toward the selected portion.

In such an arrangement, the slit image projector and laser beam projector share the common reflecting means, so that the reflecting means for the slit image projector can be arranged substantially on the same plane as the reflecting means for the laser beam projector. This makes it possible to arrange the reflecting means for the laser beam projector near to the selected portion of the eye to be coagulated and to guarantee the same aperture as in the prior art even if the reflecting means is made small. Thus, the reflecting means for the slit image projector can be made larger, thereby allowing the formation of a bright and sharp slit image with improved illumination efficiency. Moreover, the slit image projector can be arranged on the same optical axis as the laser beam projector with some optical elements shared by both projectors, thus making it possible to provide a compact laser coagulation system.

According to a preferred embodiment of the present invention, the slit image projector in the laser coagulation system includes an optical element in the form of a deflection prism arranged between a slit aperture and a condenser lens and having a roof-shaped surface one half of which serves to deflect the slit light toward one side portion of the reflecting means and the other half of which serves to deflect the slit light toward the other side portion thereof.

Such an arrangement advantageously makes it possible to form lamp filament images on the entrance pupil of an imaging lens which corresponds to the two divided side portions of the reflecting means.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENT

Figure 1:
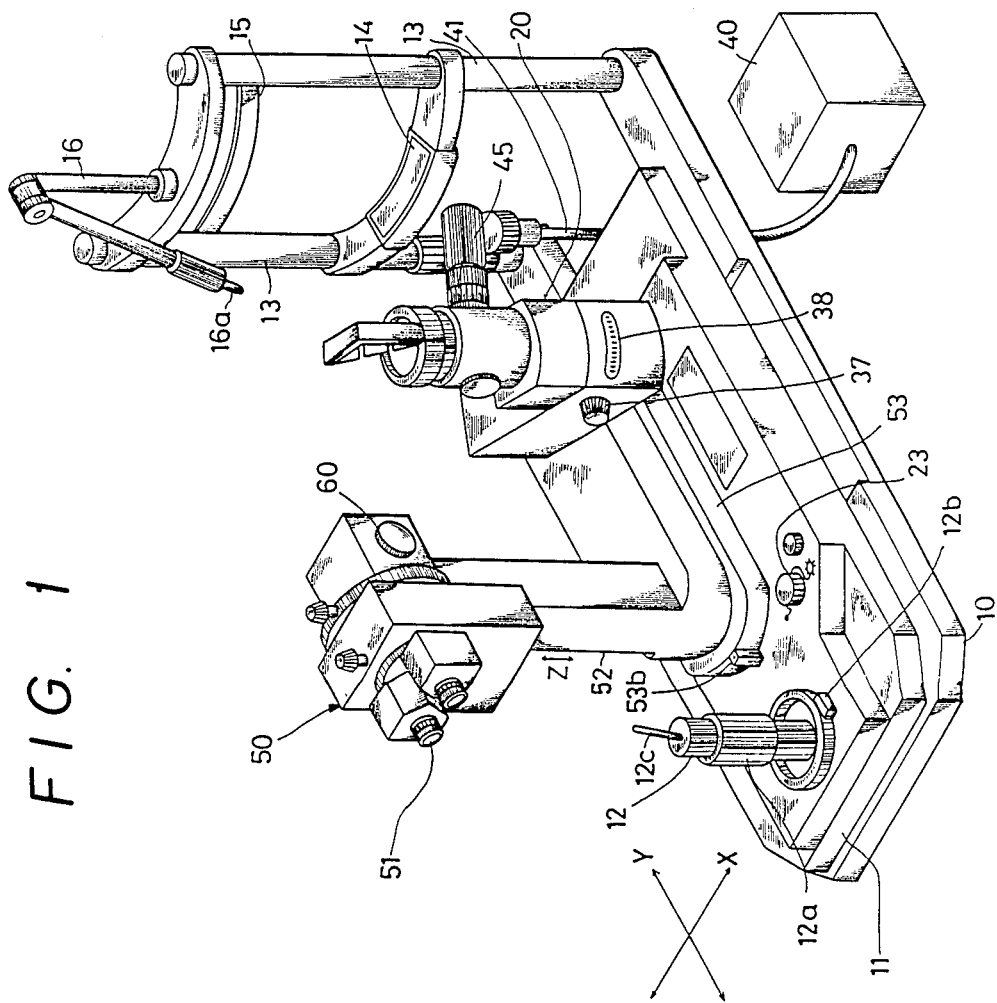
FIG. 1 is a perspective view showing the overall construction of a laser coagulation system of the present invention.

FIG. 1 shows an embodiment of a laser coagulation system according to the present invention which includes a slider 11 mounted on a base plate 10 so as to be slidable relative to the base plate 10 in a direction X or Y by means of a manipulator 12 such as a joy stick. The displacement of the slider 11 relative to the base plate 10 can be effected by operating the manipulator 12 in the directions X and Y. The slider 11 supports thereon an instrument base 53 on which are mounted a slit image projector 20, a laser beam projector 21 and an observation equipment 50 as will be fully described later. The manipulator 12 is further provided with a handle 12a, the rotation of which allows the instrument base 53 to move upwardly or downwardly in the direction Z to displace the projectors 20 and 21 together with the observation equipment 50 vertically. Thus, the manipulator 12 can adjust the position of the instrument base 53 in the directions X and Y and in the vertical direction Z. The thus adjusted slider 11 can be locked on the base plate 10 by means of a lock 12b.

The base plate 10 has on its front edge two poles 13 between which a chin support 14 and a forehead pad 15 are fixedly mounted. A patient sits down in front of the apparatus with his chin against the support 14 and his forehead against the pad 15 and directs his sight to an eye fixation lamp 16a which serves to fix the patient's eye during measurement or coagulation.

Mounted on the rear end of the slider 11 is the slit image projector 20 which is turnable about the axis A (see FIG. 2) and serves to project a slit image onto the eyeball to illuminate the background and determine the portion of the eye to be measured or coagulated. As will be described later, the slit image projector 20 is arranged coaxially with the laser beam projector 21 for projecting a laser beam from a source 40 such as an argon or krypton laser through an optical fiber 41 onto that portion to be coagulated in the eyeball. The observation equipment 50 for observing the focussed laser beam or imaged slit in the eyeball is further arranged on the front edge of the slider 11 so as to be rotated about the same axis as the turning axis A for the slit image projector 20.

Figure 2:
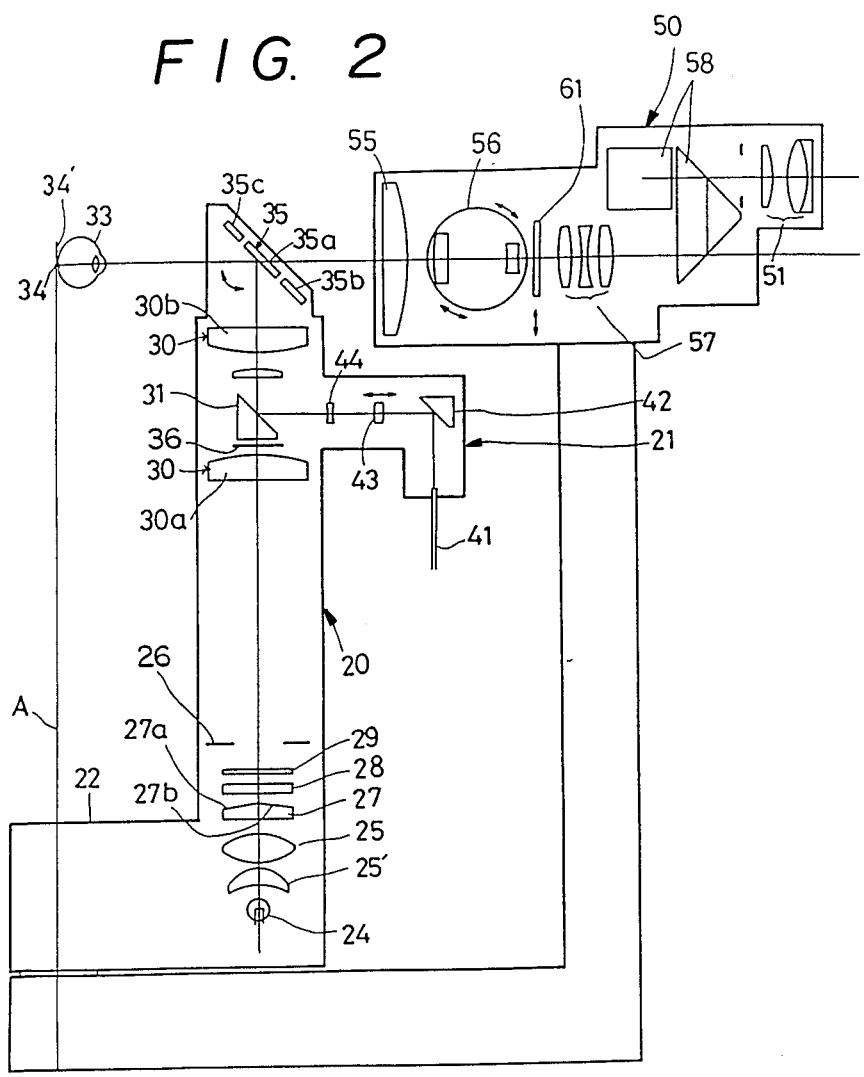
FIG. 2 is an illustrative view showing the arrangement of an optical system for a laser beam projector, slit image projector and observation equipment used in the laser coagulation system of the present invention.
Figure 3:
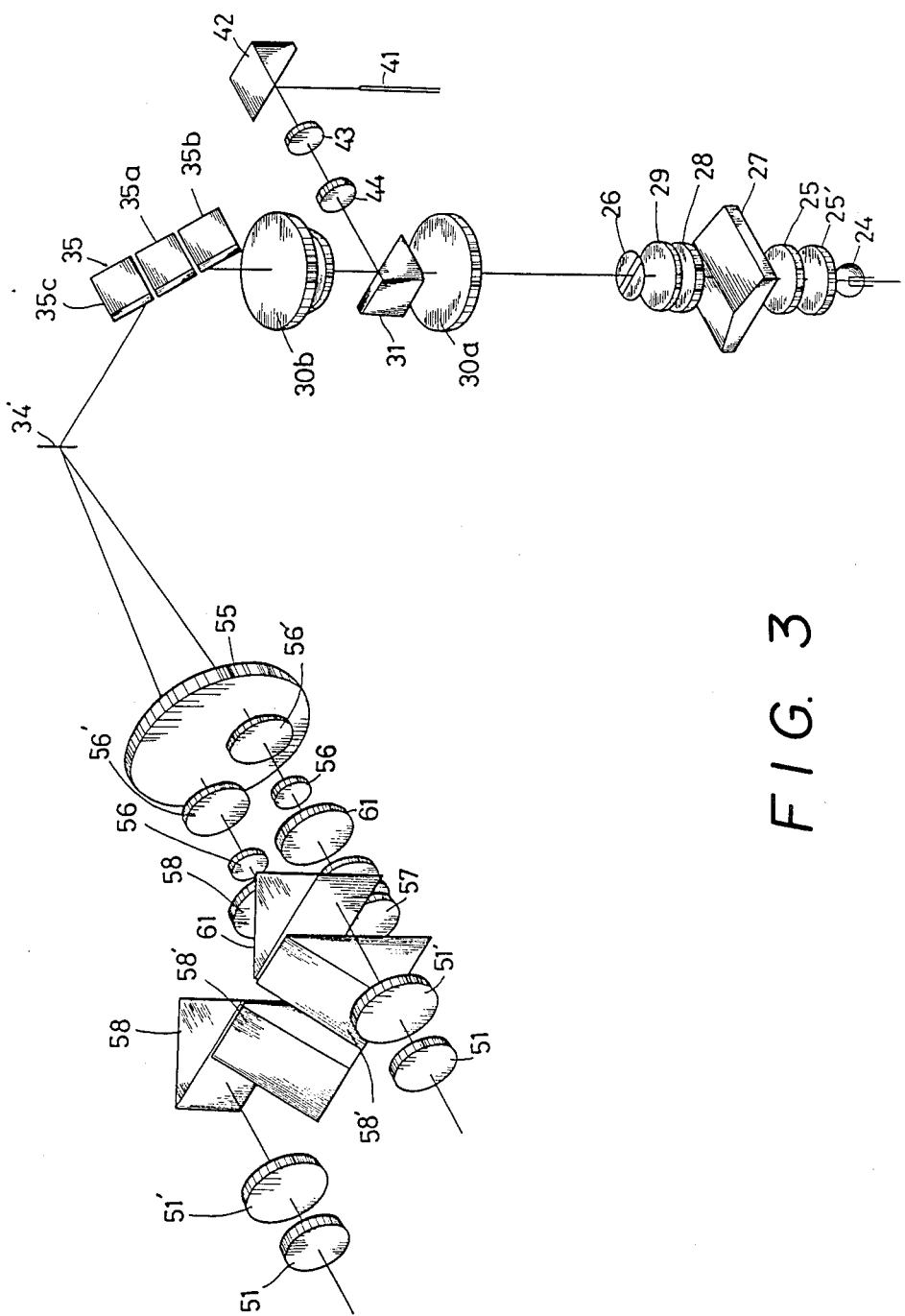
FIG. 3 is a perspective view showing the arrangement of the optical system in FIG. 2.

FIGS. 2 and 3 show the detailed arrangement of an optical system for the laser beam projector 21, slit image projector 20 and observation equipment 50. The slit image projector 20 is arranged in a housing 22 mounted so as to be rotated about the axis A and is provided therein with a lamp 24 which is adjustable in intensity by means of an adjusting knob 23 (see FIG. 1). The lamp 24 emits illuminating light, which is converged by condenser lenses 25 and 25' to illuminate a slit aperture 26. Arranged between the condenser lens 25 and slit aperture 26 are a roof-shaped prism deflection 27, an infrared ray cutting filter 28 and a detachable blue filter 29. The illuminated slit aperture 26 is imaged, for example, onto a retina 34 of a patient's eye 33 as a slit image 34' by means of a focussing lens 30 including lenses 30a and 30b. To eliminate the imaging function of the eye itself, a special contact lens (not shown) is attached to the patient's eye. A mirror assembly 35 having three-divided mirror portions 35a to 35c is mounted between the patient's eye 33 and lens 30b. The central mirror portion 35a can, as described later, be turned upwardly downwardly, leftwardly or rightwardly about an axis perpendicular to or within the paper surface (in FIG. 2) by means of an operating lever 12c of the manipulator 12.

Arranged between the lens 30a and a prism 31 is a screen plate 36 which serves to interrupt the arrival of slit light to the central mirror 35a, while permitting it to reach the lower and upper mirrors 35b, 35c to the retina 34. To make the slit image on the retina 34 brighter and sharper, the deflection prism 27 has one exit surface 27a angled to deflect light in the form of one slit image component toward the lower mirror 35b and the other exit surface 27b also angles to deflect light in the form of another slit image component toward the upper mirror 35c. Thus, the deflection prism functions to form the filament image of the lamp 24 as two slit image components at two points existing on the entrance pupil of the focussing lens 30.

It is to be noted that the slit width and length of the slit aperture 26 are adjustable by adjusting knobs 37 and 38 and the intensity of the lamp 24 by the adjusting knob 23.

The laser beam projector 21 is, on the other hand, arranged in the same housing 22 as the slit image projector 20. The laser beam passing through the optical fiber 41 from the laser source 40 is deflected rectangularly at a prism 42 toward a variator lens 43 and a lens 44, reflected at the prism 31 and then advanced along the same optical path as the slit image projector 20 through the lens 30b, mirror 35a and contact lens to radiate a laser spot of a predetermined diameter on the retina 34 for thermal coagulation. The spot diameter of the laser beam can be adjusted in the range of about 50μm to 1 mm by turning a knob 45 and adjusting the variator lens 43.

The instrument base 53 (FIG. 1) is provided with the housing 22 for accommodating the projectors 20 and 21 and a housing 52 for accommodating the observation equipment 50, and is displaceable vertically by turning the handle 12a of the manipulator 12 as mentioned before. Further, the housings 22 and 52 are turnable relative to each other about the axis A, so that the projectors 20, 21 and the observation equipment 50 can effect upward, downward or turning movement, respectively. The observation equipment 50 includes an optical system comprised of an objective 55, variator lenses 55 and 56', a safety filter 61, a focussing lens 57, erecting prisms 58 and 58', and eyepieces 51, 51'. The observation equipment 50 allows the observation of the slit image and laser spot formed in the eyeball. The adjustment of a knob 60 causes the variator lens 56 to be adjusted to provide an enlarged or reduced slit image or laser spot. The safety filter 61 is used to interrupt the laser beam reflected back from the irradiated portion of eye or cornea and protect the eyes of an observer. For this purpose, the safety filter 61 is automatically inserted into the optical path of the observation equipment 50 immediately before the laser source 40 is activated to produce a stronger laser beam.

It should be noted that, as shown in FIG. 3, the optical elements following the objective 55 are provided in pairs respectively to allow binocular observation.

The operation of the laser coagulation system according to the present invention will now be described.

The patient first sits down with his chin against the support 14 and his forehead against the pad 15 and directs his sight to the eye fixation lamp 16. The lamp 24 of the slit image projector 20 is then turned on to form the slit image 34' on the retina 34 of the patient's eye 33 through the contact lens set thereon. The slit light has its central flux inhibited from reaching the central mirror 35a by means by the screen plate 36 so that the slit light is reflected only at the lower and upper mirrors 35b and 35c to form the slit image 34' on the retina 34. In this case, the deflection prism 27 is used to deflect the slit light in the form of slit image components towards the mirrors 35b and 35c effectively. The intensity of the slit image can be adjusted by the knob 23, and the slit width and length by the adjusting knobs 37 and 38.

If the slit image 34' deviates from the desired place in the above-mentioned slit image formation, the manipulator 12 may be operated to displace the slider 11 and the housings 22 and 52 in the directions X, Y and Z and turn the projectors 20, 21 or observation equipment 50 about the axis A relative to each other until the slit image is formed on the desired portion for coagulation.

The thus formed slit image 34' can be observed by the optical system of the observation equipment including the objective 55, variator lens 56, imaging lens 57, erecting prism 58 and eyepiece 51. After the portion of eye to be coagulated has been determined, the laser source 40 is activated to emit a weak laser beam, which is caused to pass through the prism 42, variator lens 43, lens 44, prism 31, and lens 30b, reflected at the central mirror 35a and then focussed as a spot onto the retina 34. For coagulation a stronger laser beam is generated from the laser source 40 by increasing the power. When the stronger beam is activated, the safety filter is automatically inserted into the optical path of the observation equipment 50 to protect the eyes of the observer from the laser beam reflected from at the irradiated portion of the patients eye or retina.

For fine and precise coagulation, the laser spot on the retina 34 can be displaced by scanning the central mirror 35a vertically or horizontally, that is, in the direction X or Y using the operating lever 12c of the manipulator 12. The adjustment of the knob 45 allows the variator lens 43 to be displaced to adjust the spot diameter of the laser beam.

It will be appreciated that the slit image projector and laser beam projector can also share a plurality of optical elements on the condition that both the projectors are arranged on the same optical axis.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. A laser coagulation system for use in an ophthalmological treatment in which a laser beam is radiated into the eyeball of a patient to develop heat causing thermal coagulation at a selected portion in the eyeball, the system comprising
    a slit image projector for projecting a slit image into the eyeball of a patient to determine a selected portion of the eyeball to be coagulated;
    a laser beam projector for projecting a laser beam onto the selected portion of the eyeball to be coagulated in the eyeball;
    wherein both of said projectors include a common reflecting means for directing the slit image or the laser beam toward the selected portion of the eyeball, said reflecting means being divided into side portions for directing the slit image toward said selected portion and a central portion for directing the laser beam toward said selected portion; and
    the slit image projector including a slit aperture for producing slit light, a condenser lens for condensing the slit light, and a deflection prism arranged between the slit aperture and the condenser lens and having a roof-shaped surface one half of which serves to deflect the slit light toward one side portion of said reflecting means and the other half of which serves to deflect the slit light toward the other side portion thereof.

2. A laser coagulation system according to claim 1, wherein said slit image projector and laser beam projector include a common imaging lens for focussing the slit image or the laser beam on said selected portion.

3. A laser coagulation system according to claim 1, wherein the slit image projector further includes a screen plate for preventing the slit light from reaching the central portion of the reflecting means.

4. A laser coagulation system according to claim 1, wherein said central portion of said reflecting means is displaceable in a first direction to displace said laser beam in the vicinity of said selected portion in said first direction.

5. A laser coagulation system according to claim 4, wherein said central portion of said reflecting means is displaceable in a second direction perpendicular to said first direction to displace said laser beam in said second direction.

6. An apparatus for ophthalmic laser treatment of the eye of a patient, comprising: slit image projecting means for producing a slit of light and projecting a slit image into the eye of a patient to illuminate the eye to enable a determination as to the portion of the eye to be treated, the slit image projecting means including a source of light, and means for forming the light from the light source into a slit image composed of two slit image components; laser beam projecting means for projecting a laser beam into the eye of the patient for treating the eye; and wherein both the slit image projecting means and the laser beam projecting means include a common reflecting means for selectively reflecting the slit image and the laser beam toward the eye, the common reflecting means having two side portions positioned to reflect and direct the respective slit image components toward the eye to illuminate the eye, a central portion positioned to reflect and direct the laser beam toward the eye to treat the eye, and means mounting the central portion of the reflecting means to undergo displacement along at least one axis relative to the two side portions to effect scanning movement of the laser beam on the eye.

7. An apparatus according to claim 6; wherein both the slit image projecting means and the laser beam projecting means includes a common focussing means for selectively focussing the slit image and the laser beam on a selected portion of the eye.

8. An apparatus according to claim 6; wherein the means for forming the slit image composed of two slit image components comprises a slit aperture for producing a slit of light, and an optical element cooperative with the slit aperture to form a slit image composed of two slit image components.

9. An apparatus according to claim 8; wherein the optical element comprises a prism having one exit surface portion effective to direct one slit image component to one of the two reflecting means side portions and another exit surface portion effective to direct the other slit image component to the other of the two reflecting means side portions.

10. An apparatus according to claim 9; including means for preventing slit light from impinging on the central portion of the reflecting means.

11. An apparatus according to claim 10; wherein the means for preventing comprises a screen plate positioned to intercept the slit light and prevent the same from reaching the reflecting means central portion.

12. An apparatus for ophthalmic laser treatment of the eye of a patient, comprising: slit image projecting means for producing a slit of light and projecting a slit image into the eye of a patient to illuminate the eye to enable a determination as to the portion of the eye to be treated, the slit image projecting means including a source of light, and means for forming the light from the light source into a slit image composed of two slit image components; laser beam projecting means for projecting a laser beam into the eye of the patient for treating the eye; wherein both the slit image projecting means and the laser beam projecting means include a common reflecting means for selectively reflecting the slit image and the laser beam toward the eye, the common reflecting means having two side portions positioned to reflect and direct the respective slit image components toward the eye to illuminate the eye, and a central portion positioned to reflect and direct the laser beam toward the eye to treat the eye; and means for preventing slit light from impinging on the central portion of the reflecting means, the means for preventing comprising a screen plate positioned to intercept the slit light and prevent the same from reaching the reflecting means central portion.

13. An apparatus according to claim 12; wherein the central portion of the reflecting means is mounted to undergo displacement along at least one axis to effect scanning movement of the laser beam on the eye.

* * * * *